United States Patent [19]

Seite

[11] Patent Number: 5,656,940

[45] Date of Patent: Aug. 12, 1997

[54] APPARATUS FOR MEASURING THE SURFACE RESISTANCE AND ELECTRICAL RESISTIVITY OF A HOMOGENEOUS RESISTIVE MATERIAL AT HIGH TEMPERATURE

[75] Inventor: François Seite, Pessac, France

[73] Assignee: Commissariat a l'Energie Atomique, Paris, France

[21] Appl. No.: 530,147

[22] PCT Filed: Jan. 27, 1995

[86] PCT No.: PCT/FR95/00096

§ 371 Date: Sep. 25, 1995

§ 102(e) Date: Sep. 25, 1995

[87] PCT Pub. No.: WO95/20760

PCT Pub. Date: Aug. 3, 1995

[30] Foreign Application Priority Data

Jan. 28, 1994 [FR] France .................................. 94 00957

[51] Int. Cl.$^6$ ............................. G01R 27/14; G01N 27/04
[52] U.S. Cl. ......................... 324/715; 324/724; 324/717; 324/149
[58] Field of Search ...................... 324/713, 715–719, 324/724, 149, 754, 765

[56] References Cited

U.S. PATENT DOCUMENTS 4,267,506 5/1981 Shiell .................................. 324/719 X
4,888,546 12/1989 Berry et al. .......................... 324/715
5,138,269 8/1992 Deutsch ............................... 324/715

FOREIGN PATENT DOCUMENTS 2296971 7/1976 France .
2690743 11/1993 France .

OTHER PUBLICATIONS

Plenum Publishing Corporation, Apr. 1990, Industrial Laboratory, vol. 55, No. 10, A translation of Zavodskaya Laboratriya.

Primary Examiner—Maura K. Regan
Assistant Examiner—Diep Do
Attorney, Agent, or Firm—Cesari and McKenna

[57] ABSTRACT

Apparatus for measuring the surface resistance and electrical resistivity of a homogeneous, resistive material sample includes a measuring cell having a sample location able to receive the sample and several electrodes in the form of knives placed on the same side of the sample and guided in an insulating block whose ends are positioned on the sample, the pressure necessary for establishing good electrical contacts between the electrodes and the sample being ensured by a shim which urges the electrodes toward the sample. A first pair of the electrodes make it possible to inject a current into a sample to be tested and a second pair of the electrodes make it possible to collect a voltage from the sample.

6 Claims, 5 Drawing Sheets

APPARATUS FOR MEASURING THE SURFACE RESISTANCE AND ELECTRICAL RESISTIVITY OF A HOMOGENEOUS RESISTIVE MATERIAL AT HIGH TEMPERATURE

DESCRIPTION

1. Teachnical Field

The present invention relates to an apparatus for measuring the surface resistance and electrical resistivity of a homogeneous resistive material at high temperatures.

2. Prior Art

French patent application 92 05448 of May 4 1992 describes a cell for measuring the electrical resistivity at high temperature and is used exclusively for measuring the electrical resistivity of an undeformable, solid, homogeneous sample. This system has two upper and lower blocks facing one another, each matched by a horizontal face equipped with a pair of wires and between which the sample is positioned.

French patent application 92 10635 of Sep. 7 1992 describes an apparatus for measuring the surface resistance and electrical resistivity on fibers and fabrics at high temperatures. Appropriate solely for strip-like materials (fabrics) or fiber or wire-like material, the device consists of positioning the sample to be tested on a ceramic cylinder and surrounding it with four conductive wires able to maintain it level with grooves and measure the same.

Reference is made hereinafter to publications dealing with the subject of electrical resistivity and surface resistance measurement:

- article entitled (in German) "Electrical measurements on thin films at high temperatures" by G. Beddies and W. Bretschneider (Experimentelle Technik der Physik, East Germany, DA 1986, vol. 34, No. 5, pp 375–377);
- article entitled "A four point probe cell for resistivity measurement at high temperature" by A. M. George and I. K. Gogolakrishnan (Journal of Physics 1975, vol. 8, No. 1, pp 13–16);
- article entitled "Equipment developed for static high temperature resistivity measurements" by Sandra and H. Suvinsky (Scientific Instruments, 1975, vol. 46, No. 4);
- EP-A-0 337 117;
- U.S. Pat. No. 4,763,064.

None of the apparatuses described in the above documents makes it possible to perform surface resistance and electrical resistivity measurements on thin conductive films (which may or may not be deformable) deposited on insulating supports. Thus, the specificity of these apparatuses limits their use to one type of rigid or deformable, homogeneous material.

The invention relates to an apparatus for measuring the surface resistance and electrical resistivity, particularly at a high temperature (e.g. 1250° C.) of samples such as thin films deposited on insulating supports (quartz, ceramic, fabric, etc.), said apparatus being able to operate under a neutral atmosphere and accessorily under air.

DESCRIPTION OF THE INVENTION

The invention relates to an apparatus for measuring the surface resistance and electrical resistivity of a homogeneous, resistive material sample, characterized in that it comprises a measuring cell having a location able to receive said sample, as well as several electrodes in the form of aligned knives, placed on the same side of the sample and guided in an insulating block, whose ends are positioned on the sample, the pressure necessary for establishing good electrical contacts being ensured by gravity by means of a bevelled shim, two first electrodes making it possible to inject a current into the sample to be tested and two second electrodes making it possible to collect a voltage thereon.

Advantageously the measuring cell can be disassembled into two half-shells, two shouldered spindles permitting disassembly.

Advantageously, the electrodes are Invar knives, guided in an insulating block sufficiently thick to ensure a constant spacing. The rear portion of the electrodes is attached to an articulated system constituted by two brackets and an end fitting, shouldered spindles ensuring the mechanical connections. The bevelled shim bears on the end fitting and has a groove for guiding said end fitting, the weight of the shim having been calculated so as to ensure by gravity a good electrical contact between the electrodes and the sample. Electric current supply and voltage sampling leads travelling in a suspension tube are laser welded to said electrodes. This suspension tube, as well as the complete measuring cell, are made from a ceramic material able to withstand high temperatures and which is both mechanically stable and electrically insulating.

In an advantageous embodiment, the measuring cell is placed in a first quartz enclosure, in which it is possible to vary the pressure, said first enclosure being placed in a second enclosure, in which it is possible to vary the temperature.

Advantageously, the apparatus according to the invention, by its very design, is able to test all resistive material types, apart from liquids and powders, at high temperatures. As a result of its unversality, it is a very important surface resistance and electrical resistivity measuring means, in view of the fact that hitherto it has been necessary to have two types of devices for performing such a measurement.

In an exemplified embodiment, said apparatus has the following advantageous characteristics:

- the alumina measuring cell ensures a good electrical insulation and a zero porosity and by its construction in the form of two dismantlable parts instrumentation is easy, as is access to all the parts constituting the system;
- the electrical contacts, formed by Invar electrodes have a thickness close to 2 mm and are bevelled to a radius of 0.5 mm on the sample side, said thickness avoiding any high temperature deformation and ensures a very good punctiform contact;
- the guidance of the electrodes in four slots machined in a thick alumina block with a spacing of 6 mm ensures an excellent positioning of the electrical contacts on the sample, said spacing being the result of a series of experiments making it possible to optimize, with the aid of curves, the path of the current lines in the material and advantageously, it also limits the size of the samples to 20 mm×10 mm;
- the articulated bracket-end fitting means, fixed to the rear part of the electrodes, ensures, no matter what the surface state of the sample, an excellent contact between the electrodes and the latter and no matter whether the materials are rigid or flexible, they are tested under optimum conditions;
- the bearing force generator is very simple, being a bevelled shim or wedge acting by gravity, so that as a result of its shape it is able to intercalate samples of varying thickness without any complimentary setting;

the positioning of the samples, brought about by means of the shoulder of the lower portion of a cutout formed for this purpose, facilitates the fitting thereof.

DETAILED DESCRIPTION OF EMBODIMENTS

Figure 1:
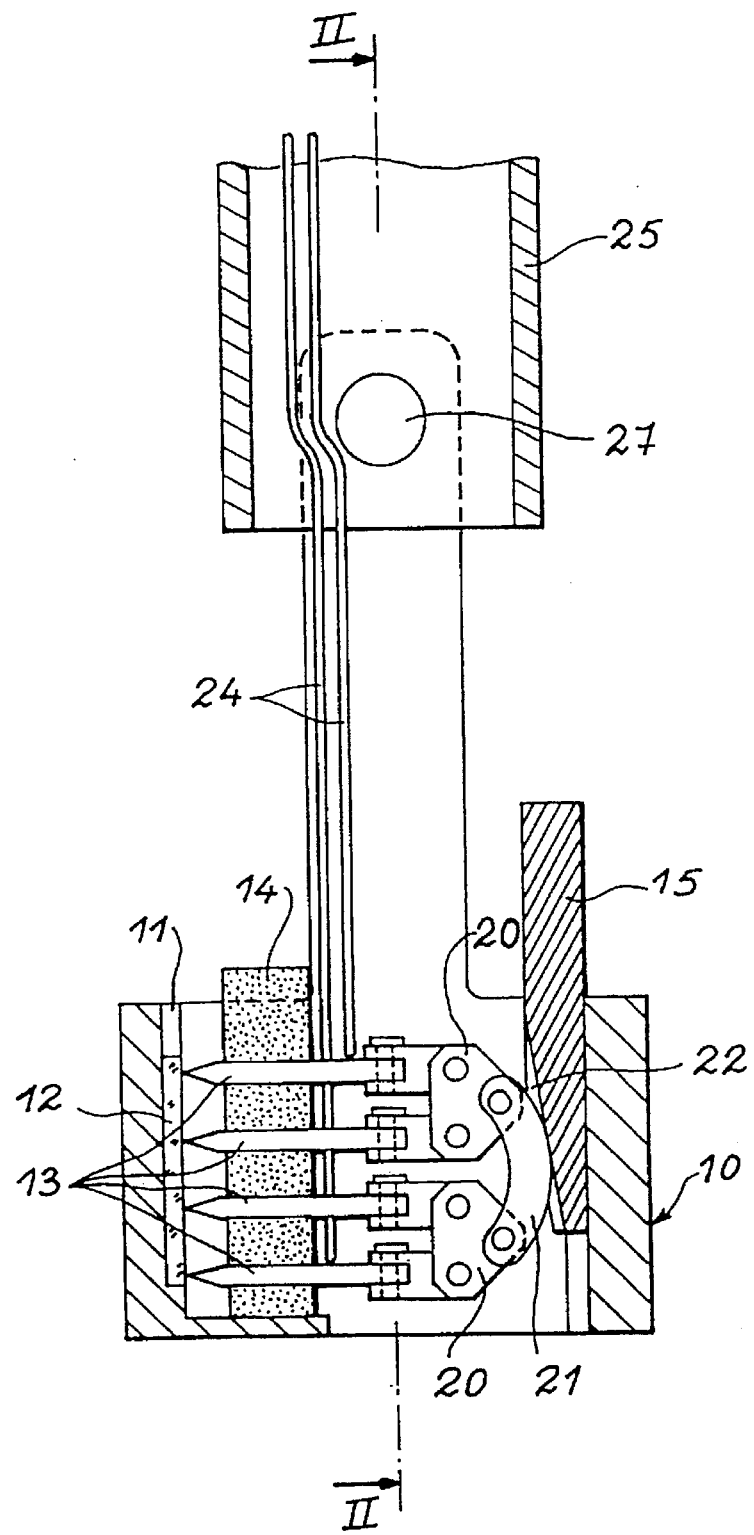
FIGS. 1 and 2 are sectional views of the measuring cell according to the invention, respectively in a longitudinal section and in a section along plane II—II of FIG. 1.
Figure 2:
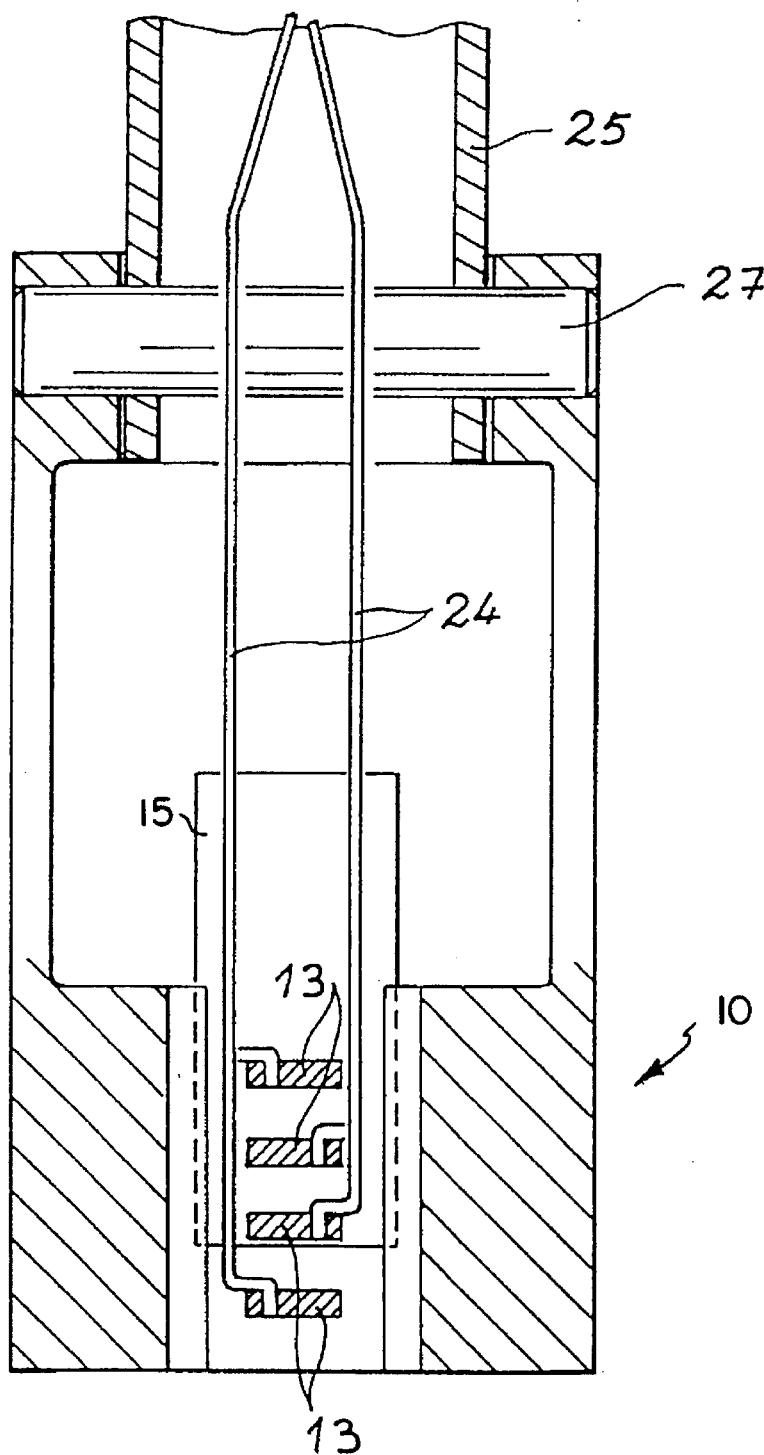

The apparatus for measuring the surface resistance and electrical resistivity of a homogeneous, resistive material sample according to the invention comprises a measuring cell 10 shown in FIGS. 1 and 2. Said cell 10 has a location 11 able to receive a sample 12 and several electrodes 13 in the form of aligned knives, placed on the same side of the sample and guided in an insulating block 14, whose ends are positioned on the sample 12, the pressure necessary for establishing good electrical contacts being ensured by gravity by means of a bevelled shim or wedge 15. Two first electrodes make it possible to inject a current into the sample to be tested and two second electrodes make it possible to collect a voltage thereon. The measuring cell 10 can be dismantled into two half-shells 16, 17, shown in FIG. 3, two shouldered spindles permitting the disassembly thereof.

In an particularly advantageous embodiment, the electrodes 13 are Invar knives, guided in the insulating block 14, e.g. of alumina, which is sufficiently thick to ensure that they have a constant spacing.

The rear portion of the electrodes is attached to an articulated system constituted by two brackets 20 and an end fitting 21, shouldered spindles ensuring the mechanical connections. The bevelled shim 15 bears on the end fitting 21 and has a groove 22 for guiding the latter, the weight of said shim 15 being calculated so as to ensure, by gravity, a good electrical contact between the electrodes 13 and the surface of the sample 12. Electric leads 24 for supplying current and sampling voltage and travelling in a suspension tube 25 are welded to said electrodes 13.

The suspension tube 25 and the complete measuring cell are made from a ceramic material able to withstand high temperatures, which is mechanically stable and electrically insulating. The suspension tube 25 is joined to the measuring cell 10 by means of a spindle 27.

Figure 3:
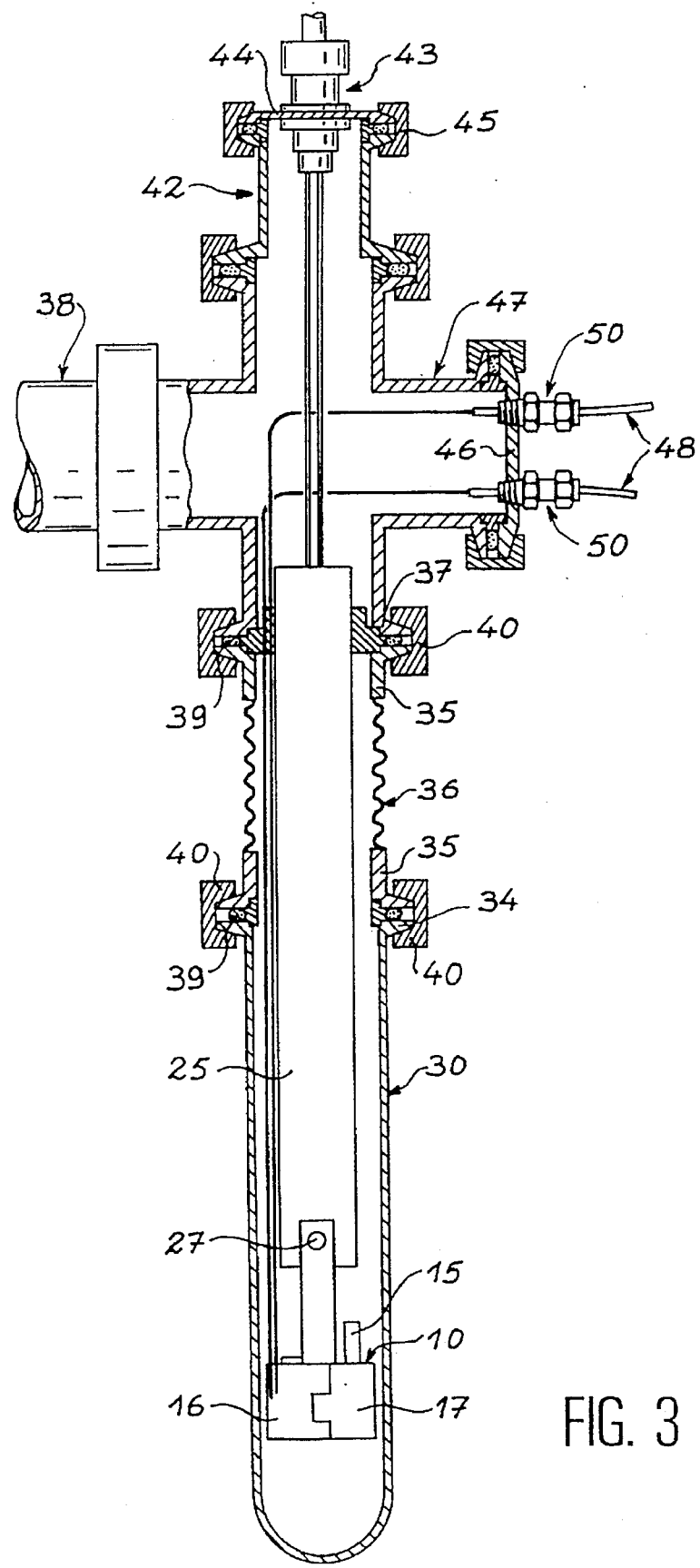
FIG. 3 illustrates a longitudinal sectional view of the first enclosure containing the measuring cell shown in FIGS. 1 and 2.
Figure 6:
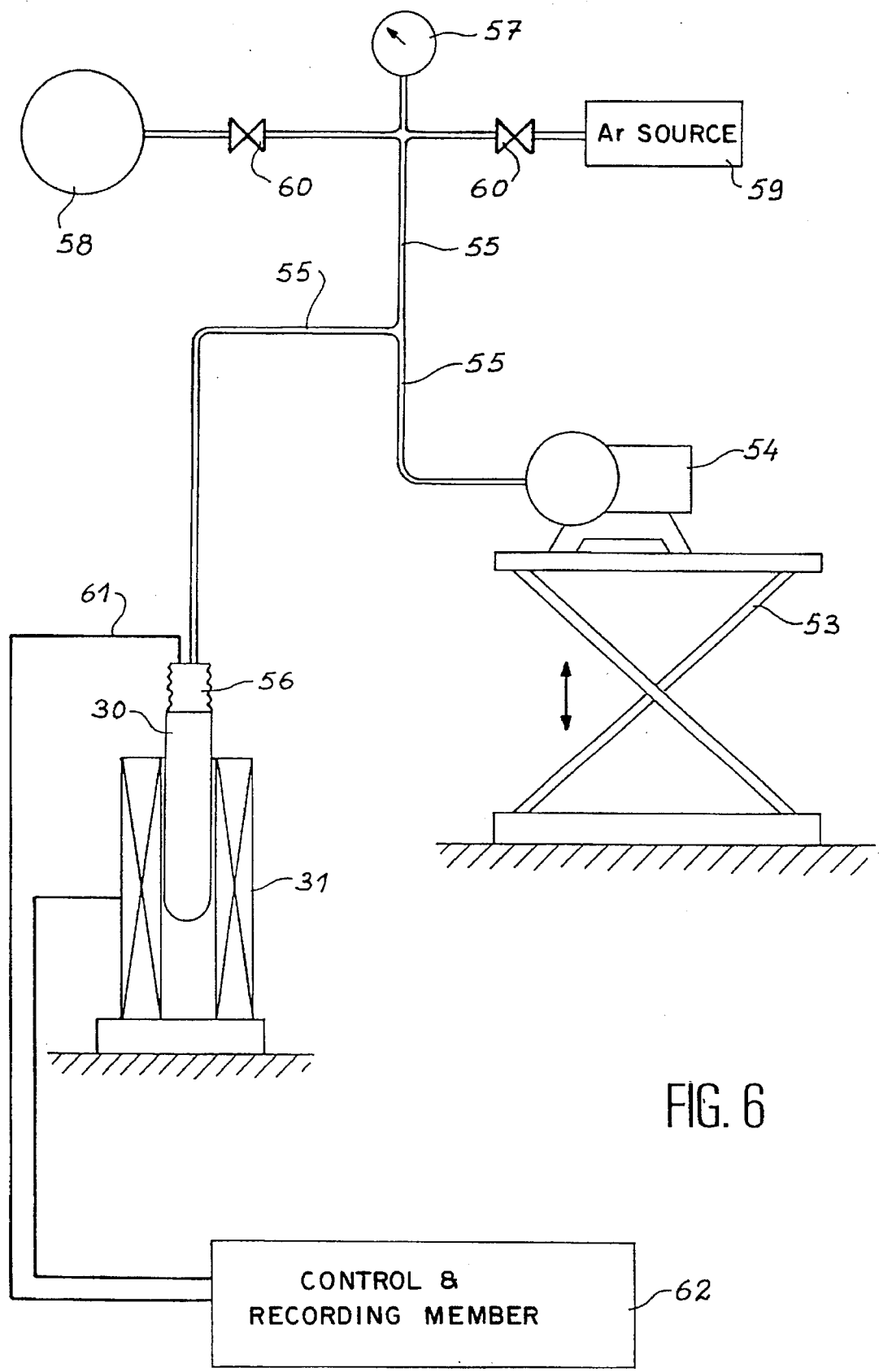
FIG. 6 illustrates the block diagram of the apparatus according to the invention.

As shown in FIG. 3, the measuring cell 10 is located in a first, cylindrical, quartz enclosure 30 sealed at one of its ends and in which it is possible to vary the pressure. As shown in FIG. 6, said enclosure 30 is placed in a second enclosure 31, in which it is possible to vary the temperature.

In an exemplified embodiment, the sample 10 is previously cut to the dimensions 25 cm×8 cm×e for electrical resistivity measurements and 25 cm×6 cm×e for surface resistance measurements, e being the thickness thereof.

Figure 4:
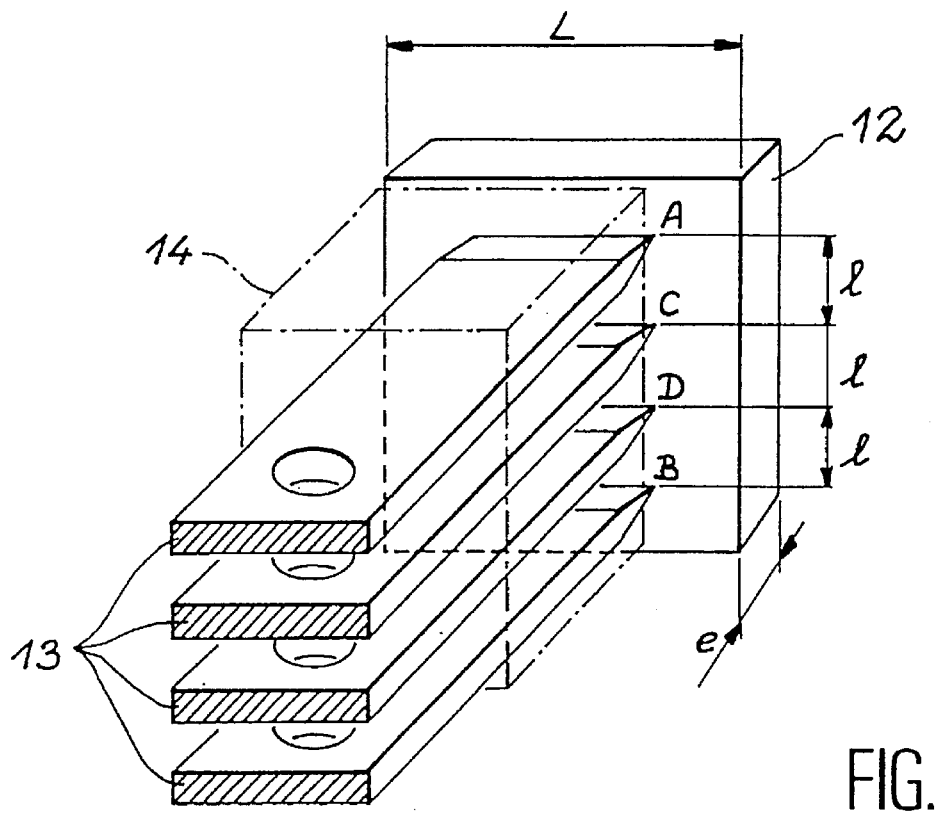
FIG. 4 illustrates the positioning of the electrodes.

The invention, as shown in FIG. 4, makes use of four Invar knives having a thickness of 2 mm so as to avoid any deformation and which serve as electrodes. They are guided in an insulating ceramic block and whereof the rounded ends are positioned on the sample 12, positioned in its location 11, facing the said electrodes 13. The pressure necessary for establishing good electrical contacts is ensured by the bevelled shim bearing on the bracket-end fitting system articulated to the rear part of the electrodes.

The invention relates to an apparatus for measuring the surface resistance and electrical resistivity on thin films and at high temperatures, designed so as to operate under a neutral atmosphere and accessorily under air. It is designed for performing measurements on conductive deposits applied to insulating supports (quartz, ceramic, fabric, etc.). However, as a result of its original design, it can also be used for measuring deformable or non-deformable, homogeneous resistive materials.

The use temperatures are between 20° and 1250° C. As a function of the sample type, the measuring ranges are as follows:

thin films of known thickness on an insulator: $\rho=10^{-8}$ to $10^{4}$ $\Omega.m$;

non-deformable, homogeneous solid: $\rho=10^{-8}$ to $10^{4}$ $\Omega.m$;

conductive fibers: $\rho=10^{4}$ to $10^{7}$ $\Omega.m$;

metallized fabrics of unknown thickness: $\rho/e=5.10^{-4}$ to $10^{6}$ $\Omega/\square$.

The dimensions of the sample and the spacing of the electrodes have been defined by calculation, as a result of a sequence of tests, in order to optimize the accuracy of the results and appear below:

sample dimensions:
  thin films on rigid or deformable support: 25×10×e (mm) (e=thickness of substrate+metallization: between 0.1 and 2 mm),
  rigid or deformable, homogeneous materials: as above,
  fibers, wires, length between 25 and 30 mm;
spacing of the electrodes: 6 mm.

As described in the aforementioned French patent application 92 05448 of Apr. 5, 1992 and as shown in FIG. 3 sealing between the enclosure 30 is ensured by means of two flanges 35 located at the ends of a bellows 36, which cooperate with a flange 34 located at the top of the enclosure 30 and a flange 37 located at the end of a system of ducts 38 for compressing circular seals or gaskets 39. Collars 40, formed from two articulated portions and provided with conical, internal surfaces complimentary of conical, external surfaces of the flanges 34, 35 and 37 ensure the locking.

The duct system 38 has an appendage 42, where the electric wires follow tight passages 43 screwed to a blind flange 44, flanged to the appendage 42 by a collar 45.

A blind flange 46 is also provided on another appendage 47 of the duct system 38. It has partition passages 50 to enable the wires connected to a control and recording member to pass into the enclosure 30 without compromising the sealing of the latter. The wires 48 lead to thermocouples, which measure the temperature close to the sample placed in the enclosure 30.

Figure 5:
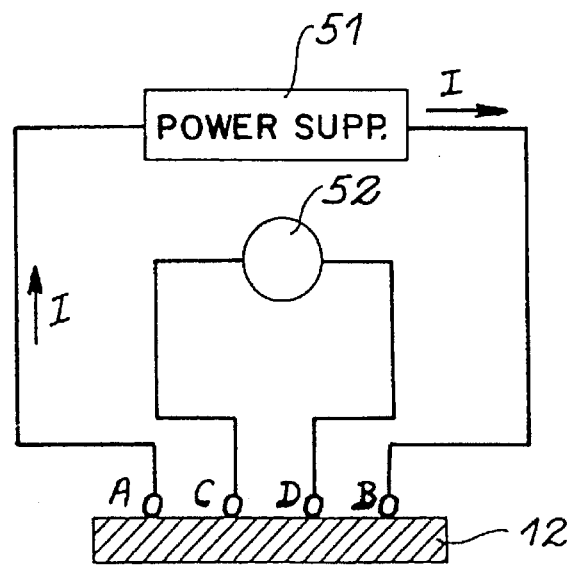
FIG. 5 illustrates the measuring principle.

The principle of the invention, illustrated in FIGS. 4 and 5, consists of injecting a constant current I from a stabilized power supply 51 into the conductive material to be tested, four equidistant electrodes A, B, C, D being placed on the same side of the sample and bear thereon.

The current I is applied through electrodes A and B, spaced e.g. by 18 mm, to the sample surface, whilst the electrodes C and D, spaced e.g. by 6 mm, collect the voltage on the same face, the measurement being performed by a voltmeter 52. The width of the electrodes is e.g. 8 mm. The choice of the dimensions is based on current line experiments.

The electrical resistivity or surface resistance is calculated as a function of the imposed current and the collected voltage. The conductive layer (in the form of a metallization) or the mass material are assumed to be homogeneous. The width of the sample is e.g. 10 mm, except in the case of fibers or wires.

The type of sample undergoing the test defines the calculation and several cases can arise:

a) Thin conductive film of known thickness, deposited on an insulating support, or deformable or non-deformable, homogeneous mass material, e.g. chromium deposit on quartz, ferrite MnZn (homogeneous mass material) and carbon fabric.

With these three examples the measurement of the electrical resistivity is based on the formula $$\rho = K \times \frac{U}{I}, \text{ with } K = \frac{S}{l} \text{ and } S = e \times L:$$

ρ: electrical resistivity l: spacing between electrodes (6 mm), e: thickness of film or sample, homogeneous material, L: sample length I: current injected between the electrodes A and B, U: voltage collected between the electrodes C and D.

b) Thin conductive film of non-measurable thickness on insulating support, e.g. an insulating fabric metallized on one side. It is a question of measuring the surface resistance ρ/e. The calculation formula for ρ/e is based on the volume resistivity formula:

$$\rho = R \times \frac{S}{L} \text{ with } R = \frac{U}{I} \text{ and } S = e \times l \text{ (width)}$$

The formula becomes:

$$\rho = \frac{U}{I} \times \frac{e \times l}{l} \frac{\text{(width)}}{\text{(difference)}}$$

In the considered case, the sample width L is 6 mm. The spacing of the electrodes 1 is also 6 mm, so that the measured sample zone represents a square.

Therefore the formula can be expressed as follows:

$$\frac{\rho}{e} = \frac{U}{I}.$$

ρ/e: surface resistance in ohm/square (ρ/□)

I: direct current injected between electrodes A and B,

U: voltage collected between the electrodes C and D.

c) Conductive fiber

The stabilized direct current is injected between the electrodes A and B and a voltage is recovered between the electrodes C and D. The fiber is positioned vertically and centred with respect to the width of the electrodes. The principle of the resistivity calculation is the same as hereinbefore, namely:

$$\rho = K \times \frac{U}{I}$$

As it is a fiber or wick, it is necessary to measure the cross-section of a filament and count the number of filaments forming the fiber. On the basis of this information, it is possible to calculate the coefficient K:

$$K = \frac{S}{l}$$

with

S: filament cross-section×number of filaments l: electrode spacing, i.e. 6 mm.

As I and U are known parameters, it is possible to calculate the volume resistivity of a fiber in the same way as a film of known thickness.

These three application examples illustrate the universality of the apparatus according to the invention, which is able to replace several specific apparatuses.

The block diagram Of the invention shown in FIG. 6 has, apart from the actual measuring cell, located in the enclosure 10, an elevating table 53 to which is fixed a vacuum pump 54, which is connected to the enclosure 30 by a duct system 55 and by a stainless steel bellows 56. The ducts 55 also lead to a manometer 57, to a balloon flask 58 for maintaining a constant pressure in the enclosure 30 and to an argon source 59. Valves 60 located on the ducts 55 make it possible to establish the desired connections, no matter whether this is for sucking or blowing in argon, for modifying the pressure or for reestablishing normal atmosphere.

The enclosure 30 is a vertical cylinder, whose bottom is closed and which can be engaged to a greater or lesser extent in a cylindrical kiln 31 as a result of vertical displacements of the table 53, or conversely can be extracted therefrom. The measurement takes place by means of electrical wires 61 partly engaged in the enclosure 30 and connected to a control and recording member 62.

The elevating table 53, whose function is to facilitate the putting into place and removal of the sample, supports the quartz enclosure 30, in which is placed the measuring cell according to the invention. This enclosure is lowered into a vertically positioned, annular kiln 31, so that the testpiece is in the centre of the kiln in the testing position. The stainless steel bellows 56 compensates alignment deficiencies of the enclosure with respect to the kiln.

The oxygen in the atmosphere of the enclosure 30 is removed by a succession of vacuum pumping operations, followed by argon fillings. The oxygen level descends to below 5 ppm. The neutral gas pressure in the quartz enclosure 30 is set, prior to the test, to approximately 1 bar. The possible overpressure, resulting from the temperature rise, is discharged to the buffer balloon flask 58, which is also responsible for insulating the installation with respect to the ambient air.

The test can then commence. The temperature rise gradient required is between 3° and 5° C./minute. The control takes place with the aid of the control and recording member 62, e.g. a microcomputer, which controls the following operations:

control of a PID-type controller making it possible to obtain a good accuracy (0.5% on a full scale of 1250° C.) and a very good temperature range stability;

application of the stabilized direct current to the electrodes A and B, as well as voltage sampling at the terminals of the electrodes C and D, the current direction being reversed on six occasions with an interval of a few seconds between them, the voltage used being the mean of six + and − readings;

processing the data from the test: curve ρ=f(t) or, as a function of the case, ρ/e=f(t).

Following a final measurement, the exploitation of the curves which takes place as from the return to ambient conditions, gives information on the variations of the electrical characteristics of the tested material and establishes whether its structure has undergone any permanent change.

The apparatus according to the invention is also designed to operate at negative temperatures. It is then merely necessary to use an enclosure 31 in the form of a cryostat.

I claim:

1. Apparatus for measuring the surface resistance and electrical resistivity of a homogeneous, resistive material sample, said apparatus comprising a measuring cell having a sample location able to receive a sample;

at least four electrodes having corresponding first and second ends;

support means in said cell for movably supporting the electrodes opposite the sample location so that said first electrode ends can be positioned on a sample at the sample location, and shim means vertically movably positioned in said cell opposite said electrode second ends so that when a sample is positioned at the sample location, gravity acting on the shim means causes the shim means to urge the electrodes against the sample to achieve good electrical contacts whereby a first pair of said electrodes enable injection of a current into the sample and a second pair of said electrodes enable a collection of a voltage from the sample.

2. The apparatus defined in claim 1 wherein the measuring cell comprises two mating half shells.

3. The apparatus defined in claim 1 wherein the support means include an electrically insulating block;

the electrodes comprise knives slidably received in said block, said knives being sufficiently thick to ensure a constant spacing thereof.

4. The apparatus defined in claim 3 and further including a first bracket mounted to the second ends of said first pair of electrodes;

a second bracket mounted to the second ends of said second pair of electrodes, and an end fitting pivotally connected between said first and second bracket, said shim means bearing against said end fitting and said end fitting having a groove for guiding the shim means for vertical movements in the cell.

5. The apparatus defined in claim 4 and further including a suspension tube;

a first pair of wires connected respectively to said first pair of electrodes;

a second pair of wires connected respectively to said second pair of electrodes, said first and second pairs of electrodes extending along said suspension tube, said cell and said suspension tube being of a mechanically stable, electrically insulating ceramic material.

6. The apparatus defined in claim 1 and further including a first enclosure enclosing said cell;

means for varying the pressure in the first enclosure;

a second enclosure enclosing the first enclosure, and means for varying the temperature in the second enclosure.

* * * * *